United States Patent [19]

Namikawa et al.

[11] Patent Number: 5,643,551
[45] Date of Patent: Jul. 1, 1997

[54] SMALL ANIMAL METASTASIS MODEL

[75] Inventors: Reiko Namikawa, Palo Alto, Calif.; Seishi Kyoizumi, Aki-gun, Japan; Emilya Shtivelman, Belmont; Joseph M. McCune, San Francisco, both of Calif.

[73] Assignee: Systemix, Inc., Palo Alto, Calif.

[21] Appl. No.: 329,679

[22] Filed: Oct. 26, 1994

Related U.S. Application Data

[63] Continuation of Ser. No. 53,063, Apr. 26, 1993, abandoned, which is a continuation-in-part of Ser. No. 27,148, Mar. 4, 1993, abandoned.

[51] Int. Cl.$^6$ .......................... A01N 57/00; A61K 38/00; C12N 5/00; C12N 15/06
[52] U.S. Cl. .......................... 424/9.1; 424/9.2; 424/93.1; 424/93.3; 424/520; 424/529; 424/578; 424/582; 424/900; 435/172.3; 800/2
[58] Field of Search .................................. 424/9.2, 93.7, 424/577, 557, 549, 573, 9.1, 93.1, 93.3, 520, 529, 578, 582, 900; 800/2, DIG. 2, DIG. 5; 435/172.3

[56] References Cited

FOREIGN PATENT DOCUMENTS

| 469632A1 | 2/1992 | European Pat. Off. |
| 93/02687 | 2/1993 | WIPO. |

OTHER PUBLICATIONS

T. Nomura et al (1991) Jpn. J. Cancer Res. 82:701–709.
R. Namikawa et al (1990) J. Exp. Med. 172:1055–1063.
S. Kyoizumi et al (1992) Blood 79(7):1704–1711.
Briles and Kornfield (1978) Isolation and metastatic properties of detachment variants of B16 melanoma cells. J Natl Cancer Inst 60(6):1217–1222.
Hart (1979) The selection and characterization of an invasive variant of the B16 melanoma. Am J Pathol 97(3):587–600.
Poste, et al. (1980) In vitro selection of murine B16 melanoma variants with enhanced tissue–invasive properties. Cancer Res 40:1636–1644.
Bresalier, et al. (1987) A new animal model for human colon cancer metastasis. Int J Cancer 39:625–630.
Morikawa, et al. (1988) In vivo selection of highly metastatic cells from surgical specimens of different primary human colon carcinomas implanted into nude mice. Cancer Res 48:1943–1948.
Morikawa, et al. (1988) Influence of organ environment on the growth, selection, and metastasis of human colon carcinoma cells in nude mice. Cancer Res 48:6863–6871.
Fu, et al. (1991) Models of human metastatic colon cancer in nude mice orthotopically constructed by using histologically intact patient specimens. Proc Natl Acad Sci USA 88:9345–9349.
Naito, et al. (1986) Growth and metastasis of tumor cells isolated from a human renal cell carcinoma implanted into different organs of nude mice. Cancer Res 46:4109–4115.

Fidler, et al. (1990) Orthotopic implantation is essential for the selection, growth and metastasis of human real (sic) cell cancer in nude mice. Cancer and Metastasis Rev 9;149–165.
Mueller, et al. (1991) Suppression of spontaneous melanoma metastasis in scid mice with an antibody to the epidermal growth factor receptor. Cancer Res 51:2193–2198.
Giavazzi, et al. (1986) "Metastatic behavior of tumor cells isolated from primary and metastatic human colorectal carcinomas implanted into different sites in nude mice." Cancer Research 46:1928–1933.
Giavazzi, et al. (1986) Experimental nude mouse model of human colorectal cancer liver metastases. J Natl Cancer Inst 77(6):1303–1308.
McCune, et al. (1988) The SCID–hu mouse: a model for the analysis of human hematolymphoid differentiation and function. Science 241:1632–1639.
Namikawa, et al. (1988) Infection of the SCID–hu mouse by HIV-1. Science 242:1684–1686.
McCune, et al. (1990) Suppression of HIV infection in AZT–treated SCID–hu mice. Science 247:564–566.
Shih, et al. (1991) Post–exposure prophylaxis with AZT suppress HIV-1 infection in SCID–hu mice in a time–dependent manner. J Inf Disease 163:625–627.
Kaneshima, et al. (1991) HIV infection of human lymph nodes in the SCID–hu mouse. Proc Natl Acad Sci USA 88:4523–4527.
Krowka, et al. (1991) Human T cells in the SCID–hu mouse are phenotypically normal and functionally competent. J Immunol 146:3751–3756.
Vandekerckhove, et al. (1991) Clonal analysis of the peripheral T cell compartment of the SCID–hu mouse. J Immunol 146:4173–9.
Kyoizumi, et al. (1992) Implantation and maintenance of functional human bone marrow in SCID–hu mice. Blood 79:1704–1711.
Vandekerckhove, et al. (1992) Human hematopoietic cells and thymic epithelial cells induce tolerance via different mechanisms in the SCID–hu mouse thymus. J Exp Med 175:1033–1043.
McCune, et al. (1989) The SCID–hu mouse: current status and potential applications. The SCID mouse, characterization and potential uses. Current Topics in Microbiology and Immunology 152;183–193 (Bosma, MJ, Schuler, W eds.). Springer–Verlag, Berlin Heidreberg.

(List continued on next page.)

*Primary Examiner*—Brian R. Stanton
*Attorney, Agent, or Firm*—Pamela J. Sherwood; Fish & Richardson PC

[57] ABSTRACT

A method for initiating metastasis of human tumor cells under experimental conditions is provided. Immunocompromised non-human mammals having a viable, xenogeneic organ or tissue are used as a host for human tumor cells. The cells are introduced into the chimeric animal after the solid tissue is implanted and are then able to grow and metastasize as they would in situ. Therapeutic regimens may be evaluated in this system to determine efficacy against metastatic processes.

5 Claims, No Drawings

OTHER PUBLICATIONS

McCune, et al. (1989) The SCID–hu mouse: A small animal model for HIV infection and antiviral testing. Progress in Immunology vol. VII:1046–1049 (Melchers F, et al.), Spring–Verlag Berlin.

McCune, et al. (1990) The SCID–hu mouse as a model system for HIV infection. Human Retroviruses, pp. 347–359.

McCune, et al. (1990) Preclinical evaluation of antiviral compounds in the SCID–hu mouse. AIDS: anti–HIV agents, therapies and vaccines. New York Academy Science, New York, NY vol. 616 edit:281–286 by Georgiev, V and McGowan, J.

McCune, et al. (1990) Psuedotypes in HIV infected mice. Science 250:1152–1153.

Kaneshima, et al. (1990) Today's SCID–hu mouse. Nature 348:561–562.

McCune, et al. (1991) The SCID–hu mouse: a small animal model for HIV infection pathogenesis. Ann Rev Immunol vol. 9 (ed. Paul, W):399–429, Annual Review Inc., Palo Alto, CA.

SMALL ANIMAL METASTASIS MODEL

CROSS-REFERENCE TO RELATED APPLICATIONS

This is a continuation of application Ser. No. 08/053,063 filed Apr. 26, 1993, now abandoned, which is a continuation-in-part of application Ser. No. 08/027,148 filed Mar. 4, 1993, now abandoned.

INTRODUCTION

1. Technical Field

The field of this invention is immunocompromised mammals comprising xenogeneic tissue, and their use in the analysis of metastasis.

2. Background

One of the most serious problems that faces a practicing oncologist is the metastasis of malignant tumor cells from the primary site to multiple, distant sites. Surgery is often effective against a primary tumor, but cannot excise all malignant tissue if the cancer has metastasized.

Existing studies aimed at understanding the mechanisms of tumor metastasis have used rodent neoplasms as a model system. It has not been possible to experimentally study human neoplasms in vivo for moral and ethical reasons. Attempts have been made to study heterotransplantation systems in which human malignant cells have been transplanted into a subcutaneous site on nude mice, but they rarely produce metastatic tumors.

However, recent studies have shown the importance of the site of implantations in xenografts. When human tumors are implanted into the correct anatomical site of nude mice, (for example, renal carcinoma cells into kidney, or colon cancer cells into spleen or cecum), then metastases can be produced. This suggests that interactions between malignant cells and the surrounding organ environment may regulate metastatic activity.

It is desirable to have an animal model for human tumors where the malignant cells could grow and move between human organ systems. This would allow anti-metastatic drugs and therapies to be evaluated under controlled and reproducible conditions.

Relevant Literature

The isolation and metastatic properties of B16 melanoma cells are described in Briles and Kornfield, J. Natl. Cancer Inst., 60, 1217 (1978). A discussion of invasive variants of this cell line may be found in I. Hart, Am. J. Pathol., 97, 587–600 (1979), and G. Poste, et al., Cancer Research, 40, 1636–1644 (1980).

The metastatic properties of colorectal carcinomas are discussed in R. Giavazzi, et al., (1986), R. Bresalier, et al., Int. J. Cancer, 39, 625–630 (1986), and the selection of metastatic variants found in K. Morikawa, et al., Cancer Research, 48, 1943–1948 (1988), and K. Morikawa, et al., Cancer Research, 48, 6863–6871 (1988). X. Fu, et al., P.N.A.S. 88, 9345–9349 (1991), describes models of human metastatic colon cancer in nude mice which are orthotopically constructed with intact patient specimens.

Other models for the growth of human tumors in nude and scid mice can be found in S. Naito, et al., Cancer Research, 46, 4109–4115 (1986), I. Fidler, et al., Cancer and Metastasis Reviews, 9, 149–165 (1990), and B. Mueller, et al., Cancer Research, 51, 2193–2198 (1991); Giavazzi, et al., ibid., 46, 1928–1933 (1986); Morikawa, et al., Cancer Research, 48, 6863–6871 (1988).

SUMMARY OF THE INVENTION

Methods, compositions and animals are provided for initiating metastasis of human tumor cells under experimental conditions. The phenomena associated with metastases may thereby be evaluated to determine the efficacy of agents and/or conditions, both prophylactic and therapeutic, against such metastatic events.

Non-human mammals are characterized by being immunocompromised, and having a viable, human xenogeneic organ or tissue which is capable of being colonized with human metastatic cells. Tumor cells are introduced into the chimeric animal after the normal human tissue is implanted. The tumors are then able to grow and metastasize as they would in the human host.

DESCRIPTION OF THE SPECIFIC EMBODIMENTS

Methods, compositions and animals are provided where immunocompromised mammals have viable human xenogeneic tissue. The healthy normal human tissue provides a growth environment for human tumor cells which allows a progression of neoplastic and metastatic events to take place. Therapies, particularly applied to the host, and drugs directed against tumor growth and metastasis can be evaluated in a controlled and reproducible manner. Also, the mechanism of metastasis and the molecules playing a role in the metastatic process may be studied.

Immunocompromised mammalian hosts having the desired immune incapacity exist or can be created. The significant factor is that the immunocompromised host is incapable naturally, or in conjunction with the introduced organs, of mounting an immune response against the xenogeneic tissue or cells. Therefore it is not sufficient that a host be immunocompromised, but that the host may not be able to mount an immune response after grafting, as evidenced by the inability to produce competent B-cells, particularly plasma cells, and/or T-cells, particularly $CD4^+$ and/or $CD8^+$ T-cells. Of particular interest are hosts, e.g. mice, which are immunocompromised in lacking functional syngeneic B and T lymphocytes as a result of a genetic defect in immunoglobulin and T-cell receptor gene rearrangement. Hosts which are presently available include hosts which have severe combined immunodeficiency, known as scid/scid, Rag-1$^-$ and/or Rag-2$^-$ hosts, which lack recombinase competence due to introduction of a genetic defect at the indicated loci.

The host will usually be of an age less than about 25% of the normal lifetime of an immunocompetent host, usually about 1 to 20% of the normal lifetime. Generally, the host will be at least about three weeks old and large enough to manipulate for introduction of the donor mammalian cells at the desired site. For example, mice are used at about 3 to 10, usually 4 to 8 weeks of age. Growth of the tissue within the host will vary with the organ.

The mammalian host will be grown in conventional ways. Depending on the degree of immunocompromised status of the mammalian host, it may be protected to varying degrees from infection. In some instances a sterile environment or prophylactic antibiosis may be indicated. Prophylactic antibiosis may be achieved for SCID mice with 25–75 mg trimethoprim and 100–300 mg sulfamethoxazole in 5 ml of suspension, given three days each week. Alternatively, it may be satisfactory to isolate the potential xenogeneic hosts from other animals in germ-free environments after caesarean derivation. The feeding and maintenance of the chimeric host will for the most part follow conventional techniques.

Various sites may be selected for the introduction of the primate, particularly human, tissue. Preferably, the sites will be downstream from a convenient site in the blood or lymphatic system for introduction of the tumor cells. In addition, the sites should provide for vascularization, and, preferably, lymphatic vessel connection as well. Sites which have found application include the popliteal fossa, kidney capsule, cervical region, particularly the outer region, peritoneal cavity, subcutaneous region, mammary fat pads, and the like.

The primate tissue solid implants are able to function for long periods of time. A variety of cells may be used, including hematopoietic, stromal, lung, fibroblasts, epithelium, endothelium, neurons, stem cells, or other cells associated with particular solid organs, such as bone marrow, pancreas, appendix, tonsil, gut, lung, GALT (gut-associated lymphoid tissue), MALT (mucosa-associated lymphold tissue), tongue, mucosal tissue, adrenal gland, thymus, liver (in conjunction with thymus), central nervous system tissue, spinal cord, thyroid, pituitary gland, hypothalamus, bone, including osteoclasts and osteoblasts, muscle, including myoblasts, myocytes, neuronal tissue and the like.

The tissue may be fresh tissue, obtained within about 48 hours of death, or freshly frozen tissue, tissue frozen within about 12 hours of death and maintained at below about −10° C., usually at about liquid nitrogen temperature (−70° C.) indefinitely. The tissue may be from an organ implanted in a chimeric host, where the tissue may be removed from 2–4 weeks after implantation, or longer. In this manner, the tissue originally obtained from the host source may be greatly expanded, substantially increasing the total number of chimeric hosts which may be obtained. The tissue obtained from the chimeric host may be treated analogously to the tissue obtained from the human source.

The tissue may be provided as portions of organs or complete organs, comprising or freed from stromal elements, generally from about 0.5 to 4 mm, more usually from about 1 to 2 mm, so that the sections can easily fit into a trocar used for implantation, usually conveniently of about 15- to 20-gauge. Normally the tissue will not have been subject to culture in vitro for an extended period of time. In some cases, whole organ grafts may be transplanted by anastomosing donor and host blood vessels, lymphatic vessels, and the like.

The cells of the foreign tissue, as well as foreign dispersed cells, e.g. dispersed fetal liver, will usually be present for at least two weeks, usually at least four weeks and may be continuously present over periods of three months or more. For the most part, normal cells, tissue, and/or organs may be stably maintained and functional for at least three to six months, frequently at least 10 months.

The cells of the foreign tissue are capable of remaining viable in the immunocompetent host and will be capable of functioning in the xenogeneic host. That is, besides carrying on normal metabolic processes, the cells will respond to ligands, transduce signals, secrete appropriate products and carry on normal functions as carried on by syngeneic cells in their wild-type host. Furthermore, where organs are involved, the cells will define a tissue mass with appropriate architecture for the organ family.

Normally, the tissue which is introduced into the host will be allowed to grow and vascularize and desirably have lymphatic vessels connected before the introduction of tumor cells. Generally, at least one week will transpire, preferably at least about two weeks. Usually tumor cells will be introduced within twenty weeks of transplantation, more usually within two to ten weeks of transplantation, the period being selected to ensure that the tissue is viable prior to harvesting.

It may be desirable to have more than one type of tissue implanted to study the dissemination of cells from a primary tissue type to other organs. One would implant the primary tissue for the tumor, as well as a tissue which is a secondary site for metastasis. For example, one may implant both human lung and bone tissue, in order to study the metastasis of lung carcinoma cells to bone marrow.

The tumor cells may be any one of the different malignant tumors which arise in humans. Among the classes of tumor cells which may be studied are sarcomas, lymphomas, adenocarcinomas, SCLC (small cell lung carcinoma), neuromas, melanomas, leukemias, basal cell carcinomas, and the like. Of particular interest are those tumors which are particularly prone to metastasize to specific organs, such as SCLC, breast carcinomas, and the like.

The tumor cells may be fresh tissue, usually obtained from patient biopsy, or freshly frozen tissue which was frozen within about 12 hours of removal from the patient and stored at below about −10° C., usually at about liquid nitrogen temperature (−70° C.), or cultured cells. The tissue may be portions of organs or solid tumors, or a cell suspension.

The method of administration of the tumor cells will depend on the type of tumor cells. In some cases, particularly for cultured cells, they will be a suspension. This can be injected systemically, through any convenient vein or blood vessel, or directly into the site of the xenogeneic organ. In other cases, particularly where biopsies of solid tumors are the source of cells, it will be implanted as a solid mass, usually from about 0.5 to 4 mm, more usually from about 1 to 2 mm.

The animals will be grown after the introduction of human tumor cells in the ways previously described. The tumor cells will be allowed to grow and metastasize for periods of usually two to six months.

During the growth and metastasis of the tumor cells the animals may be treated with therapeutic regimens which will affect the rate, size or distribution of metastases. Such treatment may include agents such as neutralizing antibodies directed against adhesion molecules or growth factor receptors, or other compounds which inhibit the processes necessary for metastasis. These processes may include vascularization of the primary tumor (angiogenesis), breakdown of the extracellular matrix at the site of the primary tumor, extravasation of the malignant cells into the circulatory or lymphatic system, adhesion of malignant cells at a metastatic site, and growth or differentiation of the tumor cells. Agents which may be studied include cytotoxic agents, anti-angiogenesis agents, differentiation inducing agents, antimitotic and mitotic agents, homing inhibitors, and the like.

Phenotyping of the tumor cells to verify their origin and stage the disease progression may be performed by standard histological methods, by immunohistochemistry, antibody staining or in situ hybridization with RNA and/or DNA probes. The exact method is not critical to the invention, and will depend on the exact tumor types being studied. Other characteristics which may be studied include tumor aggressiveness, drug regimen response, changes in the phenotype and genes associated with such changes, factors associated with metastasis, etc.

HLA markers may be used to distinguish the established xenogeneic organ transplants from the tumor cells. A mismatch between the two xenogeneic tissues will provide a method for determining the origin of cells at a later date. The HLA type can be readily determined by staining with an appropriate antibody directed against any of the alleles of the human HLA locus, including Class I and Class II antigens.

The progression of disease may be quantitated by measuring the number and size of metastatic foci after growth in the chimeric animal. Such foci can be enumerated by gross histological examination of the affected tissue, or by immunohistochemical staining.

The number of tumor cells may also be estimated by calculating the percent of donor derived cells in a tissue. This can be measured by labelling the cells with a reagent specific for a host cell marker. This may conveniently be performed by HLA typing as described above.

The following examples are offered by way of illustration and not by way of limitation.

EXPERIMENTAL

I. Growth and Metastasis of Human Leukemia Cells in an Animal Host

Materials and Methods

Patient samples

Bone marrow (BM) samples from myeloid leukemia patients were obtained with informed consent. The cells from AML cases were obtained at initial diagnosis and classified according to French-American-British (FAB) criteria as M1 (3 cases), M2 (1 case), M3 (2 cases), and M4 (1 case). A patient (Pt.1) with chronic myelogenous leukemia (CML) was diagnosed to be in myeloid blast crisis (CML-BC) phase with a blast cell population of 30% in the BM sample. Mononuclear cells were isolated by Ficoll-Paque (Pharmacia) density sedimentation and were then cryopreserved in RPMI-1640 (GIBCO) containing 10% DMSO and 10% fetal bovine serum (FBS). After thawing, cells were washed with RPMI-1640 containing 10% FBS and used for flow cytometric analysis and for implantation.

SCID-hu mice.

Homozygous C.B-17 scid/scid mice (SCID) were bred, treated with antibiotics, and used when 6–8 week old. Femurs and tibias of 19 to 23 gestational week human fetuses were cut into fragments and implanted subcutaneously into SCII mice. Cell suspensions prepared from thymus of individual fetal donors were analyzed for the HLA allotypes.

Injection of leukemia cells.

After thawing, bone marrow cells of leukemia patients (0.4–2.0×10$^6$ viable cells) were resuspended in 20 ml of RPMI-1640 containing 10% FBS and injected with a microliter syringe (Hamilton Co.) directly into the human fetal bone grafts. In all cases, the bone grafts had been implanted subcutaneously 6–8 weeks prior to the injection of leukemia cells. Combinations of bone and leukemia donors were selected to be disparate for commonly distributed HLA allotypes so that the origin of the cells in human bone implant could later be traced.

In vivo passage of leukemia cells to secondary recipients was performed in a similar fashion. Cell suspensions were prepared from bones injected with leukemia cells as described below. Cells (0.5–2.0×10$^6$) were then injected into bone grafts of other SCID-hu mice with the appropriate HLA allotypes.

Antibodies.

Mouse monoclonal antibodies (MoAbs) against MHC class I antigens were directly conjugated with either FITC or PE. These included FITC-W6/32 (monomorphic HLA class I determinant), PE-MA2.1 (HLA-A2, B17), PE-BB7.2 (HLA-A2), PE-BB7.1 (HLA-B7, Bw42), and PE-MB40.2 (HLA-B7, B40)(17). FITC-anti-LeuM1 (CD15), PE-anti-LeuM9 (CD33), PE-anti-Leu12 (CD19), FITC-anti-CALLA (CD10), and FITC-anti-HLe1 (CD45) were purchased from Becton Dickinson Immunocytometry Systems.

Flow cytometry.

Single cell suspensions were prepared from human bones and/or tumors by mincing tissues with scissors in cold RPMI-1640 containing 10% FBS. Cells were then treated with ammonium chloride to lyse red blood cells and stained for immunofluorescence. Cells from mouse peripheral blood and bone marrow were examined as well. Before analysis, propidium iodide was added at a final concentration of 10 mg/ml to selectively gate out dead cells. Multiparameter flow cytometry was performed using the FACScan system. Percent leukemia cells was calculated as the percentage of patient's HLA allotype positive cells per total human cells in the individual samples. In each experiment, isotype-matched antibodies were included as negative controls.

In the experiments designed to investigate the leukemic progenitor cell activity, leukemia cells from SCID-hu mice were stained with PE-CD33 and FITC-CD15 and sorted into $CD33^+CD15^-$ and $CD33^+CD15^+$ populations. Cell suspensions were maintained at 4° C. during sorting to avoid the loss of CD15 antigen. Cells with intermediate levels of CD15 expression were not collected.

Histology.

Cytocentrifuge slides were prepared and stained with the Wright-Giemsa stain.

Administration of all-trans retinoic acid.

All-trans retinoic acid (RA) (Sigma Chemical) was suspended in absolute ethanol at an initial stock concentration of 10 mg/ml. A solution of all-trans RA was prepared freshly at every dosing by adding 23 ml of stock solution into 300 ml of distilled water and administered orally through a gavage needle twice daily (0.45 mg/day). All dilutions were performed in subdued light and the gavage syringe was wrapped with aluminum foil. Treatment was initiated when palpable tumors developed in each mouse (18, 22, and 24 weeks after injection).

Implantation Of Human Myeloid Leukemia Cells Into SCID-Hu Mice

Cryopreserved BM cells from one case of CML myeloid blast crisis and 7 cases of AML patients were directly injected into human fetal bone fragments of SCID-hu mice. The growth of human leukemia cells in injected human BM as well as mouse BM were analyzed by flow cytometry 4–56 weeks after injection. The results of primary injection are summarized in Table 1.

TABLE 1

Growth of Human Myeloid Leukemia Cells in the SCID-hu Mouse

| Patient No. | Diagnosis (FAB) | Sample (% Blast) | Number of Cells Injected | Time After Injection (weeks) | Human BM Human Cells (%) | Human BM Leukemia Cells (%)* | Mouse BM Leukemia Cells (%) | In Vivo Passage |
|---|---|---|---|---|---|---|---|---|
| 1 | CML-BC | BM (30%) | $2 \times 10^6$ | 20 | 90 | 95 | 0 | ND |
|   |   |   | $2 \times 10^6$ | 26 | 90 | 95 | ND | + |
|   |   |   | $2 \times 10^6$ | 40 | 99 | 95 | 0 | + |
|   |   |   | $4 \times 10^5$ | 14 | 70 | 40 | 0 | + |
| 2 | AML (M1) | BM (99%) | $2 \times 10^6$ | 14 | 99 | 99 | 0 | + |
|   |   |   | $2 \times 10^6$ (3)† | 16 | 99 | 99 | 0 | + |
|   |   |   | $2 \times 10^6$ (2)† | 38 | 99 | 99 | ND | + |
| 3 | AML (M1) | BM (91%) | $2 \times 10^6$ | 12 | 99 | 80 | 0 | + |
|   |   |   | $2 \times 10^6$ | 12 | 90 | 80 | 0 | + |
|   |   |   | $4 \times 10^5$ | 16 | 95 | 99 | 0 | ND |
|   |   |   | $4 \times 10^5$ | 30 | 30 | 0 | 0 | ND |
| 4 | AML (M1) | BM (85%) | $2 \times 10^6$ | 14 | 20 | 0 | 0 | ND |
|   |   |   | $2 \times 10^6$ | 56 | 0 | 0 | ND | ND |
| 5 | AML (M2) | BM (87%) | $2 \times 10^6$ | 4 | 40 | 0 | 0 | ND |
|   |   |   | $2 \times 10^6$ | 20 | 99 | 99 | ND | + |
|   |   |   | $4 \times 10^5$ | 30 | 70 | 50 | ND | ND |
|   |   |   | $4 \times 10^5$ | 30 | 70 | 0 | ND | ND |
| 6 | AML (M3) | BM (95%) | $5 \times 10^5$ | 40 | 10 | 99 | 0 | ND |
| 7 | AML (M3) | BM (75%) | $2 \times 10^6$ | 16 | 50 | 40 | 0 | ND |
|   |   |   | $2 \times 10^6$ | 36 | 99 | 99 | 0 | + |
| 8 | AML (M4) | BM (80%) | $2 \times 10^6$ | 10 | 90 | 8 | 0 | ND |
|   |   |   | $2 \times 10^6$ | 22 | 90 | 80 | 0 | + |
|   |   |   | $4 \times 10^5$ | 53 | 45 | 99 | 0 | + |

Abbreviations: FAB, French-American-British leukemia classification; BM, bone marrow; CML-BC, CML in blast crisis; ND, not done
*Percent leukemia cells was calculated as the percentage of patient's HLA allotype positive cells per total human cells in the individual samples. For Pt. 5, who was negative for antibodies against HLA allotypes used in this experiments, percent leukemia cells were calculated based on the myeloid marker analysis and scatter analysis of human cell populations.
†Cells from 3 or 2 animals were pooled and analyzed.

The growth of BM cells from a CML patient (Pt.1) was observed in 4 out of 4 animals injected (Table 1). Since Pt.1 was HLA-B7$^+$, the cells derived from this patient could be defined by HLA allotypic MoAb, MB40.2. At 14 weeks after injection, approximately 30% of the cells recovered from the human BM graft were MB40.2$^+$ CML cells while 40% were MB40.2$^{31}$ normal human hematopoietic cells of bone donor origin. At 20 weeks after injection, a tumor surrounding the bone graft was formed. The cells prepared from the tumor tissue were mostly MB40.2$^+$, Pt.1 derived cells. These CML cells contained three distinctive populations defined by combined staining with the myeloid markers, CD33 and CD15 (CD33$^-$CD15$^-$, CD33$^+$CD15$^-$, and CD33$^+$CD15$^+$). The major cell types observed in Wright-Giemsa stained cytospin preparations were blast cells and myeloid cells of eosinophilic, basophilic and neutrophilic lineage. Megakaryocytes and maturing forms of granulocytes were found infrequently. Histologic examination demonstrated that tumor tissue consisting of atypical blast cells, granulocytic cells, and megakaryocytes with nuclear abnormality replaced the marrow space completely and no normal hematopoietic foci were left. The cellular composition of CML cells defined by phenotypic analysis with CD33 and CD15 markers as well as by cytology and histology was very similar in all three animals analyzed at 20 weeks or later. Despite the extensive growth of CML cells in the human marrow, CML cells could not be detected in the mouse marrow of any of the four mice examined.

Among three cases of M1 AML injected into SCID-hu mice, two (Pt.2 and Pt.3) showed extensive growth in human marrow (Table 1). Six out of 6 SCID-hu mice injected with cells from Pt.2 produced palpable tumors around the injected human bone grafts by 14 weeks. Flow cytometric analysis revealed that the expression of the myeloid markers CD33 and CD15 on AML cells from Pt.2 before and after implantation were almost identical, with two major populations of CD33$^+$CD15$^-$ and CD33$^+$CD15$^+$ cells. These two populations were observed reproducibly in all animals with AML cells from Pt.2. The origin of the leukemia blasts was confirmed by staining with MoAb, MB40.2, which recognized Pt.2 derived cells. In this experiment, SCID-hu mice with two human bone implants in the right and left flank were used. Since AML cells were injected into only one of the grafts, spread of the leukemia cells into the uninjected human bone graft was investigated. Cells from the uninjected human bone grafts contained MB40.2$^+$ AML cells at the levels of 30–90% of recovered human cell population, whereas no AML cells were detected in the mouse marrow.

Growth of AML cells was observed in 3 of 4 mice implanted with Pt.3 cells, 2 of 4 mice with Pt.5 cells, and 3 of 3 mice with Pt.8 cells (Table 1). The HLA types of these cells were confirmed to be of patient origin, except for those of Pt.5 who was negative for the allotypic antibodies tested. Blast cells growing in human marrow in SCID-hu mice expressed the CD33 antigen, proving their myeloid origin. None of the mice examined had leukemia cells in their marrow.

Cells from two cases of AML diagnosed as M3 were also implanted (Table 1). After thawing, only $7 \times 10^5$ viable cells were recovered from BM cells of patient Pt.6 and $5 \times 10^5$ cells were injected into one SCID-hu mouse. Analysis performed at 40 weeks demonstrated that only 10% of the cells recovered from the graft were of human origin. However, most of these cells had the characteristics of the injected AML cells, i.e., CD33$^+$CD15$^+$ phenotype, scatter profile of blast cells, and the HLA allotype of Pt.6 (HLA-B7). Cells from another M3 case M3 (Pt.7) were successfully implanted in 2 of 2 animals injected. The cells growing in the SCID-hu mice maintained the HLA type of Pt.7 (HLA-A2) detected by MoAbs MA2.1 and BB7.2. The surface phenotype of the blast cells growing in the SCID-hu mice stained with MoAbs CD33 and CD15 was similar to that of the BM cells analyzed prior to injection. Cytological features of promyelocytic leukemia cells were also maintained with abundant azurophilic granules in the cytoplasm.

In summary, in all but one case (Pt.4), detectable growth of myeloid leukemia cells was observed reproducibly in the injected human BM. Histological examination at early time points demonstrated localized growth of leukemic blast cells inside the marrow cavity co-existing with normal hematopoietic cells. Palpable tumors grew around the bone implants in animals injected with the cells from Pt.1, 2, 3, 5, 7 and 8. Macroscopically, these tumors had a greenish color regardless of the subtype in the FAB classification. The bone fragments could still be observed in the center part of the tumors by histology. Cell suspensions freshly prepared from these tumors could successfully be transferred into human bone grafts of secondary SCID-hu host by direct injection (Table 1). The surface phenotype and cytological features of the leukemia cells were stably maintained in the secondary passages. Cells from the peripheral blood of tumor-bearing animals were analyzed by flow cytometry with various combinations of antibodies reacting to myeloid leukemia cells. No tumor cells could be detected by this method except for two animals with the secondary passage of Pt.3 cells. In these animals, 1% and 4% of total nucleated cells in the peripheral blood were positive for CD33 and the HLA allotype of Pt. 3 (MA2.1 and BB7.2).

Movement and Growth of Human AML Cells in Human Bone Marrow Implanted in SCID Mouse Leukemia cells obtained from bone marrow of AML patients (stored in liquid nitrogen in an appropriate condition) were thawed and $2 \times 10^6$ viable cells were injected directly with Hamilton syringe into human fetal bone, subcutaneously implanted in SCID mice. The HLA types of the leukemia cells and bone donor were examined with antibodies specific to commonly distributed HLA allotypes, such as HLA-A2 and HLA-B7. Combinations of leukemia donor and bone donor were selected so that they could be discriminated by HLA markers. The animals were implanted with two pieces of fetal bone from the same donor subcutaneously in distans, 8–10 weeks before injection of the tumor cells. Leukemia cells were injected in only one of the bones so that the movement of the leukemia cells between two bones could be observed later.

Animals were analyzed 3–8 months after the injection of leukemia cells. Single cell suspensions were prepared from individual bone fragments and from a mouse femur, stained with antibodies against various antigens for detecting the injected human AML cells including the HLA allotypes of the patient type, and analyzed by FACS. Almost all of the cells recovered from the injected bone were shown to be positive for the HLA type of the injected leukemia cells. They were also positive for the myeloid marker CD33 and had the morphological characteristics of AML cells. Approximately 50% of the human cells recovered from the uninjected human bone were positive for antibodies reacting to the AML cells, indicating the leukemic cells had moved from the injected bone, and those metastasized cells had then grown inside the uninjected human bone marrow. In the mouse bone marrow of the same animal, human leukemia cells could not be detected. Leukemia cells from 5 AML patients gave similar results, i.e., leukemia cells spread into human marrow in a distant site but not into mouse bone marrow.

These results demonstrate that species-specific malignant cell movement and growth can be observed reproducibly in this animal model.

Treatment Of M3 Leukemia Cells With All-Trans Retinoic Acid

Three SCID-hu mice bearing M3 leukemia cells from Pt.8 (passage 2) were treated with all-trans RA at a dose of 0.45 mg/day given orally twice a day. This dose was selected based on that used clinically (45 mg/m2/day) assuming a mouse body surface area of 100 $cm^2$. Phenotypical and cytological changes of leukemia cells were examined after 3 to 9 days of treatment. In normal myeloid differentiation pathways, maturation towards the granulocytic lineage is characterized by the acquisition of the CD15 antigen. In vitro experiments with cells from M3 patients showed that CD15 could be a suitable marker for the differentiation of promyelocytic leukemia cells. Since most of the blast cells of Pt.8 were $CD33^+CD15^-$, one can predict that the expression of the granulocytic differentiation antigen, CD15 might be induced by RA treatment.

In the experiments described here, the percentages of $CD33^+CD15^-$ cells and $CD33^+CD15^+$ cells were normalized to a total of 100% $CD33^+$ cells. A small piece of the tumor (secondary passage) was biopsied on day 3 of treatment and analyzed. No significant changes in the expression of CD15 or in cytology were observed in comparison to the original cells and controls (primary and secondary passage cells without treatment). On the 7th day of treatment, the mouse was sacrificed for analysis. A significant portion of leukemia cells (27%) were positive for CD15 at this timepoint (Table 2). Similar results were obtained from two other SCID-hu mice with secondary passage cells. The population of $CD15^+$ cells increased to 14% and 54% after 7 and 9 days of treatment, respectively. Induction of granulocytic differentiation was confirmed by cytology. After 7 days of treatment with all-trans RA, more differentiated forms of myeloid cells with lobulated nucleus and neutrophilic granules could be observed among the promyelocytic cells. Thus, it was demonstrated that promyelocytic leukemia cells growing in the SCID-hu mouse could respond to all-trans RA and differentiate into mature neutrophilic cells.

TABLE 2

Effects of all-trans Retinoic Acid on Promyelocytic Leukemia Cells

| passage | treatment | | $CD33^+CD15^-$ | $CD33^+CD15^+$ |
|---|---|---|---|---|
| original cells | NA | | 96% | 0% |
| 1 | no | | 99% | 1% |
| 2 | no | | 99% | 1% |
| 2 | all-trans RA (0.45 mg/d) | 3 days* 7 days* | 97% | 3% |
| 2 | | 7 days | 73% | 27% |
| 2 | | 9 days | 86% | 14% |
| 2 | | | 44% | 56% |

Abbreviation: NA, not applicable
*Samples were derived from the same tumor biopsied on day 3 and day 7.

Leukemic Progenitor Cell Population in AML Blasts

As described, AML cells from Pt.2 contained two populations defined by the myeloid markers CD33 and CD15. We compared the leukemic progenitor cell activity in less mature (CD33+CD15−) and more differentiated (CD33+CD15+) populations by transferring varying numbers of sorted cells into secondary SCID-hu mice. Two independent experiments were performed with a total of 45 SCID-hu mice created from 5 bone donors. Tumor cells from 3 or 2 animals were harvested, pooled, stained with PE-CD33 and FITC-CD15, and then sorted into CD33+CD15− and CD33+CD15+ populations. Growth of leukemia was analyzed by flow cytometry 8–11 weeks after injection of $10^6$ and $10^5$ cells and 9–14 weeks with lower doses of cells. The growth of AML cells was indicated as the percentage of HLA-B7+ (MB40.2+, BB7.1+) cells among total human hematopoietic cells detected by combined staining with MoAbs, W6/32 and CD45.

The results summarized in Table 3 clearly demonstrate that the $CD33^{+CD}15^-$ population is more efficient in transferring leukemia into the secondary hosts. Five out of 5 animals injected with $10^4$ CD33+CD15− cells and 3 out of 5 animals injected with $10^3$ CD33+CD15− cells had detectable levels of leukemic cell growth whereas none of 10 animals injected with the same number of CD33+CD15+ cells showed evidence of leukemia growth. It was also observed that the leukemia which developed in the secondary hosts consistently contained both CD33+CD15− and CD33+CD15+ populations, similar to the original leukemia cells, regardless of the injected population.

TABLE 3

Comparison of Leukemic Progenitor Cell Activity in CD33+CD15− and CD33+CD15+ AML Cells

| Cell Population | Number of Cells Injected | Positive Mice | % Leukemia Cells* | | | | |
|---|---|---|---|---|---|---|---|
| unsorted | $10^6$ | 3/3 | 100, | 89, | 78 | | |
| CD33+CD15− | $10^6$ | 5/6 | 100, | 97, | 73, | 57, | 24, 0 |
| | $10^5$ | 4/6 | 100, | 73, | 63, | 17, | 0, 0 |
| | $10^4$ | 5/5 | 100, | 100, | 81, | 76, | 55, |
| | $10^3$ | 3/5 | 88, | 70, | 8, | 0, | 0, |
| CD33+CD15+ | $10^6$ | 4/5 | 100, | 95, | 9, | 1, | 0 |
| | $10^5$ | 3/5 | 95, | 53, | 45, | 0, | 0 |
| | $10^4$ | 0/5 | 0, | 0, | 0, | 0, | 0 |
| | $10^3$ | 0/5 | 0, | 0, | 0, | 0, | 0 |

These data represent the results of two independent experiments.
*Percentage of leukemia cells are expressed as the percentage of W6/32+/MB40.2+ cells among total human cells defined as W6/32+/CD45+.

II. Movement and Growth of Human Lung Cancer Cells in an Animal Model

The data below illustrate the use of SCID-hu mice as a model for the study of the metastatic spread of human solid tumors. The novelty, and major advantage of the SCID-hu model lies in the fact that it allows one to analyze the in vivo metastatic spread of human tumor cells to specific human tissues.

Cells of human lung cancer cell lines are introduced intravenously into immunodeficient SCID mice implanted prior to inoculation with fragments of human fetal lung. The specific homing and growth of tumor cells in human lung tissue is observed. Alternatively, tumor cells are introduced via direct injection into one of several human lung implants in SCID-hu, and the metastatic movement of tumor cells between lung implants observed. This model of species- and organ-specific metastasis can be used for studies of molecular mechanisms of metastasis and for development of new therapeutic modalities.

Materials and Methods

Mice and Tissues.

Homozygous CB-17 scid/scid mice were used at the age of 6 to 8 weeks. Human fetal lungs at 18 to 22 gestational week were cut into fragments approximately 1 $mm^3$ and surgically implanted into mouse mammary fat pads and under the kidney capsule. Human fetal femurs and tibias at the same gestational age were cut lengthwise and implanted subcutaneously into SCID mice. The resulting SCID-hu animals were used for experiments at 4 to 8 weeks post implantation.

Cell Lines.

Small cell lung carcinomas (SCLC) cell lines N417 and H82 of variant subtype were obtained from National Cancer Institute, National Institutes of Health. Lung adenocarcinoma cell line A427 was obtained from ATCC. Cell lines were maintained in growth medium RPMI 1640 (N417 and H82) or DMEM (A427) supplemented with 10% fetal bovine serum.

Experimental Procedures.

Tumor cells were injected into SCID-hu mice intravenously via the lateral tail vein. Alternatively, cells were injected directly into human fetal tissues implanted subcutaneously into mice. Mice were examined twice a week for growth of tumors and sacrificed at or before the time when tumor volume reached 5 $cm^3$. Human lung implants, mouse lungs and other internal organs and tumors were examined histologically. Single cell suspensions were prepared from the aseptically removed and minced tumors by incubation for 1 hour at 37° C. in the presence of dispase and DNase. Cells were washed and used for intravenous injection or explanted in vitro to reestablish cell lines.

Results

Specific Homing and Growth of Small Cell Lung Carcinoma Cell Line H82 in Human Lung Tissues.

Cells of SCLC line H82 were harvested and injected intravenously into SCID-hu mice implanted with three fetal human lung fragments, two of them in mammary fat pads and one under the kidney capsule. Mice were sacrificed at 4 to 5 weeks post injection, due to the appearance of fast growing tumors in human lung tissue. In most mice tumor growth involved all three lung implants. In no cases were tumors found in any mouse organs, including mouse lungs. This was confirmed by histological analysis of tissues.

Cell line H82T1 was reestablished in vitro from one of human lung tumors and was used for intravenous injection of SCID-hu (lung) mice. Again, this resulted in development of tumors exclusively within human fetal lung fragments. The results are summarized in Table 4. Thus, the blood-borne spread of H82 cells results in the specific growth of tumors within human lung tissue, without involvement of the mouse organs.

TABLE 4

SCLC Line H82 Metastasizes to Human Lung Tissue.

| Injected Cells | No. of Mice | No. of Implants | No. of Mice with Tumors | No. of Mice with 3 Tumors | No. of Mice with 2 Tumors | No. of Mice with 1 Tumor |
|---|---|---|---|---|---|---|
| $3 \times 10^6$ H82 | 10 | 3 | 8 | 7 | 1 | 0 |
| $10^6$ H82T1 | 5 | 2 | 4 | — | 3 | 1 |

Homing and Growth of Small Cell Lung Carcinoma Cell Line N417 in Human Lung Tissue.

N417 cells were used in experiments similar to those described above for H82 cells. We observed that N417 cells are capable of homing specifically to human lung tissue within SCID-hu mice, and that this ability is sustained after one passage in vivo. The latent period for tumor formation in human lung tissue was 4 to 6 weeks. The results are summarized in Table 5.

It is clear that N417 cells, similarly to H82 cells, migrate and grow specifically in the human fetal lung tissue. However, intravenous injection of N417 cells into SCID mice resulted in tumor growth in mouse tissues (see below). Significantly, these tumors developed after longer latent periods than the human lung tumors in SCID-hu (lung) mice. The latter reach appreciable size 4 to 6 weeks post injection, while tumors in mouse organs (preferentially in fat tissues) develop over longer periods of time, 8 to 12 weeks post injection. Thus, SCID-hu (lung) mice that received N417 cells develop human lung tumors, and have to be sacrificed before they are able to develop tumors in mouse organs.

These data show that specific metastatic movement of tumor cells from a primary tumor to other human tissue can occur in SCID-hu mice.

TABLE 5

SCLC Line N417 Metastasizes to Human Lung Tissue

| Injected Cells | No. of Mice | No. of Implants Per Mouse | No. of Mice with Tumors | No. of Mice with 3 Tumors | No. of Mice with 2 Tumors | No. of Mice with 1 Tumor |
|---|---|---|---|---|---|---|
| $2 \times 10^6$ N417 | 9 | 3 | 8 | 2 | 5 | 1 |
| $10^6$ N417T1* | 4 | 2 | 4 | — | 3 | 1 |

*Cell line N417T1 was derived from a human lung tumor induced in the SCID-hu by intravenous injection of N417 cells.

Metastatic Spread of N417 From Primary Tumor to Other Human Implants in SCID-hu.

To study the ability of N417 cells for "true" metastasis in SCID-hu mice, i.e. tumor cells which metastasize from a primary tumor to other organs, direct injection into one of human fetal implants was used. SCID-hu mice were implanted with one fetal bone fragment and two lung fragments. $10^5$ N417T1 cells were injected directly into one of the lung implants. After the tumor in the injected tissue reached significant size, mice were sacrificed and examined for presence of tumor growth in sites other than the injected tissue. The results are shown in Table 6.

TABLE 6

SCLC Line N417 Metastasizes to Human Lung Tissue.

| No. of Mice Injected in Lung Implant | Tumors in Injected Lung | Mice with Tumors in Uninjected Lung | Mice with Tumors in Bone Implant | Time Post Injection |
|---|---|---|---|---|
| 10 | 10 | 5 | 0 | 4–7 w |

TABLE 6-continued

SCLC Line N417 Metastasizes to Human Lung Tissue.

| No. of Mice Injected in Bone Implant | Tumors in Injected Bone Implant | Mice with Tumors in One of Lung Implants | Time Post Injection |
|---|---|---|---|
| 5 | 5 | 2 | 3–5 w |

Selection of a Bone Marrow Metastatic Variant of SCLC N417.

Bone marrow involvement is a frequent clinical feature in SCLC patients. In order to select a bone marrow metastatic variant, N417 cells were injected intravenously into SCID-hu (bone) mice. Most of these animals developed tumors in various brown fat tissue sites within 8 to 12 weeks post injection. Upon termination of the animals, the human bone marrow was retrieved, examined histologically and explanted in vitro. Out of 10 mice injected, one showed the presence of N417 cells within the human bone implant, both by histology and by the outgrowth of tumor cells in vitro. These cells were used for a second round of injection into SCID-hu mice, and showed an increased ability to migrate to human bone marrow and cause tumor growth within it. Selection of a stable variant of N417 metastatic for human bone marrow will enable the dissection of changes in tumor cell phenotype which lead to the involvement of bone marrow in metastatic spread.

Lung adenocarcinoma cell line A427.

A427 cells were injected intravenously into SCID-hu (lung) mice to examine their ability to migrate to and grow in the human fetal lung tissue. Out of a total of 54 mice that received cell injections, 6 animals (11%) developed tumors in human lung tissues over periods of time ranging from 5 to 6 months. None of the injected animals developed tumors in tissues other than the human lung tissues.

Cells were retrieved from one of the lung tumors (A427T1V) and used for the second round of in vivo passage through intravenous injection. The A427T1V cells were also explanted in vitro to establish a permanent cell line. About 80% of cells explanted in vitro died over a course of first days in culture. The resulting cell line A427T1 was injected into SCID-hu mice after several in vitro passages. The results of these experiments appear in Table 7.

It is clear from the results presented above that the parental cell line A427 has a very limited ability to migrate and/or grow in human lung tissue in SCID-hu mice. However, the first in vivo passage of A427 resulted in the selection of a variant (A427T1V) with a dramatically increased ability to invade human lung tissue. A427T1V cells induced tumors in all injected animals after a very short latency period, compared to that of the parental cell line. However, this homing capability appears to be sustained only in vivo, since it is lost after several passages of the tumor cells in vitro.

This particular feature of A427 cell tumorigenicity in human lung tissue is a unique opportunity to define the cellular factors necessary for homing to, and survival in, lung tissues of adenocarcinoma cells.

TABLE 7

Tumorigenicity of A427 Cells and Selected Variants in SCID-Hu (Lung).

| Cells | No. of Mice | Latency | No. of Mice with Tumors | No. of Mice with 3 Tumors | No. of Mice with 2 Tumors | No. of Mice with 1 Tumor |
|---|---|---|---|---|---|---|
| A427 | 54 | 5–6 m | 6 | 0 | 1 | 5 |
| A427T1V | 10 | 6–7 w | 10 | 6 | 3 | 1 |
| A427T1 | 10 | 3–4 w | 0 | 0 | 0 | 0 |

The examples of metastatic behavior for human lung cancer lines in SCID-hu mice described above illustrate the use of the SCID-hu mouse as a model to study the process of metastases of human solid tumors. In SCID-hu animals one can study both species-specific and organ-specific metastasis.

It is apparent from the results presented above that the metastatic properties of human lung cancer cells are species-specific. It is particularly striking when one considers the small size and lower vascularization of the human lung implant, compared to the mouse lungs.

Organ-specificity of metastases can be studied in SCID-hu mice implanted with fragments of different human organs. This model allows the selection of tumor cell variants with an enhanced ability to metastasize to a human tissue of interest.

This system provides a useful tool to assess the capacity of any kind of human tumor cell, regardless of the cell type, to metastasize to any human tissues that are implanted in the SCID mouse.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method to assess the effect of a treatment directed against a metastasis of human tumors, said method comprising:

applying said treatment to a chimeric mouse host, said mouse host comprising (a) an immunodeficient mouse lacking functional lymphocytes as a result of a genetic defect in immunoglobulin and T-cell receptor gene rearrangement (b), at least one solid normal functional vascularized human fetal organ tissue comprising non-neoplastic cells capable of providing an environment for the metastasis of human tumor cells, and (c) an implanted human tumor; and determining the effect of said treatment on metastasis of said human tumor to said human fetal organ tissue.

2. A method according to claim 1, where said at least one solid normal functional vascularized human fetal organ tissue comprises at least two distinct organ types.

3. A method according to claim 2, wherein said organ types are human fetal lung and human fetal bone.

4. A method for assessing the metastatic potential of a human tumor in a chimeric mouse host comprising:
  (a) an immunodeficient mouse lacking functional lymphocytes as a result of a genetic defect in immunoglobulin and T-cell receptor gene rearrangement;
  (b) a first implant comprising solid normal functional vascularized human fetal organ tissue capable of providing an environment for the growth of cells of said human tumor; and
  (c) a second implant comprising solid normal functional vascularized human fetal organ tissue capable of receiving and supporting growth of said cells of said human tumor which metastasize;

said method comprising:
  introducing cells of said tumor into said first implant;
  growing said host for a sufficient time to allow for metastasis; and
  determining the presence of said cells of said human tumor in said second implant.

5. A method according to claim 4, wherein said first implant is bone and said second implant is lung.

* * * * *